(12) United States Patent
Roulier et al.

(10) Patent No.: US 6,280,750 B1
(45) Date of Patent: *Aug. 28, 2001

(54) SOLID COSMETIC COMPOSITION AND USES THEREOF

(75) Inventors: Veronique Roulier, Paris; Eric Quemin, Tremblay en France, both of (FR)

(73) Assignee: L'Oreal, Paris (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/357,956

(22) Filed: Jul. 21, 1999

(30) Foreign Application Priority Data

Jul. 30, 1998 (FR) .................................................. 98 09793

(51) Int. Cl.$^7$ ............................ A61K 7/00; A61K 7/021; A61K 7/025; A61K 7/32; A61K 7/06
(52) U.S. Cl. .............................. 424/401; 424/63; 424/64; 424/65; 424/70.7; 424/70.13; 424/400; 424/484; 424/485; 424/486; 424/487; 424/488; 424/DIG. 5; 426/573; 514/944
(58) Field of Search ................................. 424/400, 401, 424/484, 485, 486, 487, 488, 63, 64, 65, 70.7, 70.13, DIG. 5; 514/944; 426/573

(56) References Cited

U.S. PATENT DOCUMENTS

| | | |
|---|---|---|
| 4,647,470 | 3/1987 | Sanderson et al. . |
| 4,746,528 | 5/1988 | Prest et al. . |
| 5,342,626 | 8/1994 | Winston, Jr. et al. . |
| 5,968,528 * | 10/1999 | Deckner et al. ................... 424/401 |
| 5,972,354 * | 10/1999 | De La Poterie et al. ............ 424/401 |

FOREIGN PATENT DOCUMENTS

| | | |
|---|---|---|
| 0 667 148 | 8/1995 | (EP) . |
| 0 803 245 | 10/1997 | (EP) . |
| 2738835 * | 3/1997 | (FR) . |
| 2 219 803 | 12/1989 | (GB) . |
| WO 97/17053 | 5/1997 | (WO) . |
| WO 97/17055 | 5/1997 | (WO) . |

* cited by examiner

Primary Examiner—Jose' G. Dees
Assistant Examiner—Marina Lamm
(74) Attorney, Agent, or Firm—Oblon, Spivak, McClelland, Maier & Neustadt, P.C.

(57) ABSTRACT

A solid composition for topical application comprising, in an aqueous phase, a gelling system comprising (i) gellan gum, (ii) at least one other hydrocolloid chosen from the group formed by xanthan gum, carboxymethylcellulose, hydroxypropylcellulose, methylcellulose, hydroxypropylmethylcellulose, hydroxyethylcellulose, agar-agar, carrageenans, alginates, carob gum, guar gum, gum arabic, karaya gum, gum tragacanth, ghatti gum, pectins, gelatin, caseinates and hydroxypropylguar, and (iii) at least one amphiphilic polymer comprising at least one fatty chain and at least one hydrophilic unit.

22 Claims, No Drawings

SOLID COSMETIC COMPOSITION AND USES THEREOF

BACKGROUND OF THE INVENTION

1. Field of the Invention

The present invention relates to a solid composition for topical application, as well as to its use in cosmetics and/or dermatology, in particular for conditioning and/or treating the skin, the scalp, the hair and/or mucous membranes, for making up the skin and/or keratin fibers such as the eyelashes and the hair, and for styling and/or shaping keratin fibers, and in particular the hair.

2. Description of the Background

Products in solid form are known in the cosmetics industry. Products of this type include, for example, in the field of make-up, tubes or "sticks" of lipstick, foundation or eyeshadow; in the field of skin- or lip-care, lip-repair pencils and depigmenting, make-up-removing or moisturizing tubes or "sticks"; in the field of hygiene, deodorant sticks and foaming sticks or bars for shaving or washing the skin. Solid products also include patches, which act, in particular, transdermally, for example, either to make an active agent penetrate the skin or to cleanse the skin.

Formulated sticks based on waxes have certain drawbacks: they have a greasy nature which users do not appreciate and they lack freshness when applied. In addition, it is difficult to introduce hydrophilic active agents therein.

Moreover, non-greasy sticks such as deodorant sticks generally contain a relatively large amount of fatty acid salts, which may exhibit an irritant effect in applications where care of the skin of the face is desired. Moreover, these sticks leave a sticky film after application to the skin.

Aqueous rigid gels are disclosed in the publications WO-A-97/17055 and WO-A-97/17053. However, these gels require a fairly high concentration of gelling agent or involve a specific preparation technique such as extrusion. In addition, the sticks described in publication WO-A-97/17055 lack transparency and, because of the high concentration of gelling agent, lack freshness and softness when they are applied to the skin. The sticks described in publication WO-A-97/17053 must be hydrated at the time of use.

Publication EP 0 803 245 describes aqueous solid compositions containing heat-reversible polysaccharides, a wetting agent and a powdery phase (fillers). However, the presence of a powdery phase may give rise to the drawbacks of a visible trace when the composition is applied to the skin and a reduction in the sensation of comfort of the skin. Further, when the powdery phase is removed from the composition described in the publication, a composition is obtained which is neither sufficiently solid nor sufficiently stable, and which does not give satisfactory transfer or deposition of the product on the skin. Thus, there is still a need for a solid composition for topical application to the skin which does not have the drawbacks of the prior art.

SUMMARY OF THE INVENTION

Accordingly, one object of the present invention is to provide a composition which feels fresh when applied to the skin and gives a good deposit of the product on the skin while at the same time being sufficiently solid.

Briefly, this object and other objects of the present invention as hereinafter will become more readily apparent can be attained by a solid composition, comprising, in an aqueous phase, a gelling system comprising (i) gellan gum, (ii) at least one other hydrocolloid selected from the group consisting of xanthan gum, carboxymethylcellulose, hydroxypropylcellulose, methylcellulose, hydroxypropylmethylcellulose, hydroxyethylcellulose, agar-agar, carrageenans, alginates, carob gum, guar gum, gum arabic, karaya gum, gum tragacanth, ghatti gum, pectins, gelatin, caseinates and hydroxypropylguar, and (iii) at least one amphiphilic polymer comprising at least one fatty chain and at least one hydrophilic unit.

DETAILED DESCRIPTION OF THE PREFERRED EMBODIMENTS

The discovery of the present invention is a specific gelling system based on hydrocolloids and an associative polymer for preparing homogeneous, rigid, aqueous compositions which are stable even at low contents of gelling agent, and which do not necessarily require the use of a specific technique of preparation. In addition, the gelling system permits the direct application of product onto the skin without the necessity of prewetting the skin.

An associative polymer is an amphiphilic polymer comprising at least one fatty chain, and thus a hydrophobic portion, and at least one hydrophilic unit, and thus a hydrophilic portion.

For the purposes of the present invention, the expression "solid composition" refers to any composition which has a compression strength of greater than or equal to 20 grams at room temperature (20–25° C.), after penetration with an axisymmetric probe of diameter 0.8 cm into the matrix of the composition to a depth of 1 mm at a speed of 0.5 mm/s and removal of the probe from the matrix of the composition at a speed of 0.5 mm/s. Compression strength is measured with an analyzer such as the "LFRA Texture Analyzer" sold by the company Stevens/Mechtric.

The solid composition of the invention can be applied directly to a substrate, i.e. it does not need to be made wet to be applied to the support, and in particular to the skin. The term "substrate" for the composition of the invention means any surface on which a topical application can be made, in particular the skin, keratin fibers such as the eyelashes and the hair, the scalp and mucous membranes such as the lips.

The gelling system of the invention gives, even in small amounts, a solid composition whose strength and rigidity are satisfactory while at the same time leaving a good deposit on the skin.

In addition, unlike solid compositions comprising a large proportion of powdered material, the composition of the invention has the advantage of not leaving a visible powdery deposit when it is applied to a substrate. Moreover, it has the property of being transparent or translucent in the absence of oil.

Furthermore, the solid composition of the invention has good transfer properties, i.e. when applied to a substrate, in that it releases an effective amount of product onto the substrate, while at the same time being particularly solid.

In the composition of the invention, the gellan gum is present in an amount of at least 1.5% based on the total weight of the composition, and, for example, in an amount ranging from 1.5–15%, preferably from 2–8% and better still from 2–4% by weight, based on the total weight of the composition.

In a preferred embodiment of the invention, the hydrocolloid (ii) is preferably selected from xanthan gum, carob gum, carboxymethylcellulose and hydroxypropylguar, and mixtures thereof.

The hydrocolloid(s) (ii) is (are) present in the composition of the invention in an amount which can vary within a wide range. Thus, this amount can range, for example, from 0.1–10%, preferably from 1–5% and better still from 2–4%, by weight based on the total weight of the composition.

Depending on the proportions, and in particular when the total amount of hydrocolloids (gellan plus hydrocolloid (ii)) exceeds 4%, the mixture can advantageously be prepared in a twin-screw extruder by the technique described in document EP-A-667,148.

Any associative polymer can be used in the composition of the invention as amphiphilic polymer (iii). In this amphiphilic polymer, the hydrophobic portion can be present in a reduced amount with respect to the rest of the polymer chain, can be located laterally relative to the chain and can be distributed randomly (random copolymers) or distributed in the form of sequences or grafts (block copolymers or sequenced copolymers). Moreover, water-soluble or water-dispersible polymers or alternatively water-swellable polymers can be used.

The amphiphilic polymers can be of any chemical nature; it is thus possible to choose polymers of natural origin, which are optionally modified; radical polymers, in particular vinyl or acrylic polymers; polycondensates; and mixtures thereof. They can be ionic or nonionic, and are preferably anionic or nonionic.

The amphiphilic polymers comprising at least one fatty chain and at least one hydrophilic unit, which are used in the invention, are preferably selected from the group consisting of:

(1) holosides modified with groups comprising at least one fatty chain. Modified holosides include, for example:

celluloses or derivatives thereof, modified with groups comprising at least one fatty chain such as an alkyl, arylalkyl or alkylaryl group or mixtures thereof in which the alkyl groups contains from 8–22 carbon atoms;

nonionic alkylhydroxyethylcelluloses such as the products Natrosol Plus Grade 330 CS, Polysurf 67 and ADX 410, ($C_{16}$ alkyl) sold by Aqualon;

quatemized (cationic) alkylhydroxyethylcelluloses such as the products Quatrisoft LM 200, Quatrisoft LM-X 529-18-A, Quatrisoft LM-X 529-18-B ($C_{12}$ alkyl) and Quatrisoft LM-X 529-8 ($C_{12}$ alkyl) sold by Amerchol and the products Crodacel QM, Crodacel QL ($C_{12}$ alkyl) and Crodacel QS ($C_{18}$ alkyl) sold by Croda;

nonionic nonoxynylhydroxyethylcelluloses such as the product Amercell HM-1500 sold by Amerchol;

nonionic alkylcelluloses such as the product Bermocoll EHM 100 sold by Berol Nobel;

polyalcohol ($C_{12}$–$C_{18}$) saccharides such as the product Emulsan (D-galactosamine/aminuronic acid mixture) and the product Biosan LPS-50 sold by Petroferm;

hydroxypropylguars modified with a fatty chain such as the product Esaflor HM 22 (modified with a $C_{22}$ alkyl chain), sold by Lamberti; the product Miracare XC 95-3 (modified with a $C_{14}$ alkyl chain) and the product RE 205-146 (modified with a $C_{20}$ alkyl chain) sold by Rhône-Poulenc;

(2) copolymers of maleic anhydride or of a derivative thereof and of monomers comprising at least one fatty chain. Examples which include:

N-octadecyl vinyl ether/maleic anhydride copolymers such as the product Gantrez AN-8194 sold by ISP;

vinyl acetate/isobutyl monomaleate/vinyl neodecanoate terpolymers such as the products ACV-4033 and 9649- 147 sold by ISP, the product Meypro-Fix 509 sold by Meyhall and the products Densodrin BA and Lipoderm Liquor FP sold by BASF;

(3) polyurethanes and derivatives thereof comprising groups containing at least one fatty chain such as, for example, the following commercial products:

Rheolate 204, 205, 208, 210, 255 and 278 sold by Rheox; Bermodol Pur 2130 sold by Berol Nobel; Acrysol SCT-275, Acrysol RM-870, Acrysol RM-825, Acrysol 44 and Acrysol 46, DW-1206 B, DW-1206 F, DW-1206 G and DW-1206 J sold by Röhm & Haas; Dapral T 212 sold by Akzo; SER-AD FX 1100 sold by Hüls; Borchigel LW.44 and Borchigel L.75.N sold by Borchers;

(4) copolymers of crotonic acid and of monomers comprising at least one fatty chain such as vinyl acetate/crotonic acid/allyl stearate terpolymers;

(5) copolymers of N-vinylpyrrolidone and of monomers comprising at least one fatty chain such as olefins substituted with an alkyl radical comprising a long hydrocarbon-based chain such as, for example, the products Antaron V216 and Antaron V220 sold by ISP;

(6) copolymers of (meth)acrylic acid and of monomers comprising at least one fatty chain; these monomers are selected from hydrophobic monomers containing a fatty chain, amphiphilic monomers comprising a hydrophobic portion containing a fatty chain and a hydrophilic portion, or mixtures thereof. Copolymers of this type include, for example:

crosslinked copolymers of acrylic acid/$C_{10}$–$C_{30}$ alkyl acrylate such as the products Pemulen TR 1, Pemulen TR 2, Carbopol 1382, Carbopol 1342 and Carbopol ETD 2020 sold by Goodrich;

(meth)acrylic acid/ethyl acrylate/alkyl acrylate copolymers such as the product Acusol 823 sold by Röhn & Haas and the product Imperon R sold by Hoechst;

acrylic acid/vinyl isodecanoate crosslinked copolymers such as the product Stabylen 30 sold by 3V;

acrylic acid/vinylpyrrolidone/lauryl methacrylate terpolymers such as the products Acrylidone LM, ACP-1184, ACP-1194 sold by ISP; acrylic acid/lauryl (meth) acrylate copolymers such as the products Coatex SX sold by Coatex;

(meth)acrylic acid/alkyl acrylate/polyethoxylated alkyl allyl ether terpolymers such as Rheovis —CR, —$CR_3$, —$CR_2$ and —CRX sold by Allied Colloids;

methacrylic acid/ethyl acrylate/polyethoxylated stearyl allyl ether terpolymers such as the products Salcare-SC90 and -SC80 sold by Allied Colloids;

methacrylic acid/ethyl acrylate/polyoxyethylenated lauryl acrylate terpolymers such as the product Rheo 2000 sold by Coatex;

methacrylic acid/ethyl acrylate/polyoxyethylenated stearyl methacrylate terpolymers such as the products Acrysol 22, Acrysol 25 and DW-1206A sold by Röhm & Haas;

methacrylic acid/ethyl acrylate/polyoxyethylenated nonylphenyl acrylate copolymers such as the product Rheo 3000 sold by Coatex;

acrylic acid/polyoxyethylenated stearyl monoitaconate copolymers or acrylic acid/polyoxyethylenated cetyl monoitaconate copolymers such as the products 8069-72A and 8069-72B sold by National Starch;

copolymers of methacrylic acid/butyl acrylate/hydrophobic monomer comprising at least one fatty chain such as the product 8069-146A sold by National Starch;

acrylic acid/$C_{15}$ alkyl acrylatelpolyethylene glycol acrylate (28 mol of ethylene oxide) terpolymers such as the product Dapral GE 202 sold by Akzo;

salts of a partial fatty acid ester of an acrylic acid/dimethylethanolamine copolymer such as the product Dapral GE 202 DMA sold by Akzo;

copolymers of acrylic acid/acrylate/amphiphilic monomer comprising a fatty chain containing urethane groups such as the product Additol VXW 1312 sold by Hoechst;

acrylic copolymers modified with hydrophobic groups containing a fatty chain such as the product Acusol 102 sold by Rohm & Haas;

(7) nonionic copolymers of lower ($C_1$–$C_6$) alkyl (meth)acrylate and of amphiphilic monomers comprising a fatty chain such as, for example, copolymers of methyl methacrylate/polyoxyethylenated stearyl acrylate such as the product Antil 208 sold by Goldschmidt; and (8) nonionic copolymers of hydrophilic (meth)acrylates and of hydrophobic monomers containing a fatty chain such as, for example, polyethylene glycol methacrylate/methyl methacrylate copolymers.

In a preferred embodiment of the invention, the amphiphilic polymer is more particularly selected from polyurethanes and modified holosides.

Either an amphiphilic polymer or a mixture of amphiphilic polymers can be used in the composition of the invention.

The amphiphilic polymers are used in the composition of the invention in an amount which is effective in obtaining the estimated result. The amount of amphiphlic polymer(s) preferably ranges from 0.05–20% by weight relative to the total weight of the composition. More preferably, this amount ranges from 0.1–10% by weight and even more preferably from 0.2–5% by weight relative to the total weight of the composition.

The gelling system comprising the compounds (i), (ii) and (iii) in the composition of the invention is used in an amount which is effective in obtaining the estimated result. The gelling system preferably represents from 2–30% and better still from 2–10% by weight, based on the total weight of the composition.

The aqueous phase of the composition of the invention generally represents from 60–97% and preferably from 80–95% by weight, based on the total weight of the composition.

It is possible to modify the rigidity of the compositions of the invention by adding thereto one or more salts which increase the rigidity of the composition. These salts can be selected from salts of mono-, di- or trivalent metals, and more particularly alkali metal and alkaline-earth metal salts and in particular sodium and calcium salts. The ions constituting these salts can be selected, for example, from carbonates, bicarbonates, sulfates, glycerophosphates, borates, chlorides, nitrates, acetates, hydroxides and persulphates, as well as the salts of α-hydroxy acids such as citrates, tartrates, lactates and malates or of fruit acids, or alternatively salts of amino acids such as aspartate, arginate, glycocholate and fumarate.

The salt is preferably selected from sodium, calcium, magnesium, strontium, neodymium or manganese chloride, calcium, magnesium or strontium nitrate, calcium or magnesium borate, magnesium or calcium sulfate, and calcium or magnesium acetate, and mixtures thereof The amount of salt(s) can range from 0.01–5% and preferably from 0.1–2% based on the total weight of the composition.

In a preferred embodiment of the invention, the composition also comprises at least one solvent other than water.

Suitable solvents include primary alcohols containing from 1–4 carbon atoms such as ethanol and isopropanol, glycols such as propylene glycol, butylene glycol, dipropylene glycol and diethylene glycol, glycol ethers such as mono-, di- or tripropylene glycol ($C_1$–$C_4$)alkyl ether or mono-, di- or triethylene glycol ($C_1$–$C_4$) alkyl ether, and mixtures thereof. The amount of solvent(s) can range from 0.01–20% and preferably from 0.1–5% by weight, based on the total weight of the composition.

The solid composition of the invention is advantageously a composition for topical application, in particular a cosmetic or dermatological composition. Such a composition comprises a medium which is physiologically acceptable, in particular for the skin, including the scalp, mucous membranes, the nails and/or keratin fibers (hair or eyelashes).

According to one specific embodiment of the invention, the composition also comprises at least one oil, this addition of oil giving a greater sensation of comfort when the composition is applied to the skin.

Suitable oils which can be used include mineral oils, oils of plant origin, oils of animal origin, synthetic oils such as fatty esters, silicone oils such as volatile silicone oils, polymethylsiloxanes, polymethylphenylsiloxanes, polysiloxanes modified with fatty acids, fatty alcohols and polyoxyalkylenes, fluorosilicones and perfluoro oils. Other fatty substances such as fatty acids, fatty alcohols and waxes can also be employed.

The oil(s) and the other fatty substances optionally present constitute the fatty phase.

The fatty phase can be present in proportions ranging, for example, up to 30%, preferably from 0.1–20% and better still from 0.5–10%, b y weight of the total weight of the composition, these proportions varying depending on the application selected.

The fatty phase can be introduced into the aqueous phase in the presence of one or more surfactants to ensure better dispersion.

The compositions of the invention can thus also contain one or more nonionic, anionic, cationic or amphoteric surfactants of the type usually employed in cosmetics and/or dermatology. The amounts of surfactant(s) can range from 0.05–8% and better still from 0.05–5% by weight, based on the total weight of the composition.

The compositions of the invention can also contain additives usually employed in cosmetics and/or dermatology. Suitable such additives particularly include antioxidants and free-radical scavengers, water-soluble dyes such as FD&C Red No. 4 and D&C Green No. 5, and alternatively liposoluble dyes, if the composition comprises a fatty chain, hydrophilic or lipophilic active agents, fragrances and fillers.

The active agents can be selected, for example, from hydrating or wetting agents such as polyols and in particular glycerol, UV screening agents, antidandruff agents, conditioners, deodorant active agents, depigmenting agents and bleaching agents, tensioning agents and anti-wrinkle agents, latices and pseudolatices, and any other active agent which is appropriate for finishing the solid product in question.

Suitable latices and pseudolatices include, for example, dispersions of synthetic polymers of the polycondensate type or of the radical type. Suitable polymers constituting the latex or pseudolatex include the anionic, cationic, nonionic and amphoteric polyurethanes, polyurethane-acrylics, polyurethane-polyvinylpyrrolidones, polyester-polyurethanes, polyether-polyurethanes, polyureas, acrylic polymers, acrylic copolymers, sulfonated isophthalic acid polymers and polymers resulting from the radical polymerization of one or more radical monomers. Suitable synthetic polymers which may be used in the preparation of latices include in particular the dispersions of polyester-polyurethanes and of the polyether-polyurethanes sold under the names "Sancure 2060" (polyester-polyurethane), "Sancure 2255" (polyester-polyurethane), "Sancure 815" (polyester-polyurethane), "Sancure 878" (polyether-polyurethane) and "Sancure 861", (polyether-polyurethane) by Sanncor, under the names "Neorez R974" (polyester-poly-urethane), "Neorez R981 " (polyesterpoly-urethane), "Neorez R970" (polyether-polyurethane) by ICI and the acrylic copolymer dispersion sold under the name "Neocryl XK-90" by Zeneca.

Suitable fillers include, for example, insoluble dyes, pigments and powders, and in particular, talc powders, starch powders, acrylate polymer and copolymer powders, mica powder, kaolin powder, polyamide (Nylon) powder, polyethylene powder, silica powder and silicone powder.

These additives can be present in the final composition in an amount ranging from 0–30% by weight, preferably from 0.5–20% and even more particularly from 0.5–10% by weight, based on the total weight of the composition.

Needless to say, the person of skill in the art will select the one or more optional additives and the amounts thereof for a given composition in order to obtain the advantageous properties intrinsically desired for a composition of the invention. Of course, the selection of additive(s) should not be such as to substantially, adversely affect the properties of the composition desired.

The compositions of the invention can constitute products for the care and/or conditioning and/or hygiene of the skin, mucous membranes, the scalp and/or the hair. Among the care, conditioning or hygiene products in bar, stick or pencil form, such products include, for example, hair care and solid gels for styling and/or shaping the hair; in skincare, moisturizing products, slimming products, depigmenting and bleaching products, and lipcare products; for facial and/or body hygiene, shaving products and deodorants.

Another object of the invention is a cosmetic treatment process for the care and/or conditioning and/or hygiene of the skin, the hair, the scalp and/or mucous membranes, this process consisting in applying a solid composition as defined above to the skin, the hair, the scalp and/or mucous membranes.

The compositions of the invention can also be employed in make-up products such as lipsticks, foundations, eyeshadows, blushers, concealers, mascaras, lip contour pencils, eye contour pencils or sticks for dyeing locks of hair. The compositions can, in particular, constitute "transfer-free" make-up products, i.e. products which deposit a film which, after application, does not transfer or migrate or stain a surface with which the make-up product applied to the skin may subsequently come into contact such as clothing, glass, cups, or the like.

Thus, an aspect of the present invention is also the use of the composition of the invention to formulate a transfer-free make-up product. If the make-up product also contains a latex or a pseudolatex, a product with good staying power is obtained.

An aspect of the present invention is also a process for making-up the skin and/or keratin fibers, which consists in applying a solid composition as defined above to the face, the lips, the contour of the eyes, the cheeks, the contour of the lips, the eyelashes, the eyebrows, the hair and/or the eyelids.

The composition of the invention can also constitute patches which are intended for application directly onto the skin. These patches may comprise the composition of the invention alone or incorporated in a composite structure in the form of layers, which can comprise in particular, besides the composition of the invention, a support layer and/or a detachable protective layer.

Thus, an aspect of the invention is also a patch which comprises the present composition as defined above.

Having now generally described the invention, a further understanding can be obtained by reference to certain specific Examples which are provided herein for purpose of illustration only and are not intended to be limiting unless otherwise specified. The percentages in the Examples are expressed-by weight, except where otherwise mentioned.

Example 1: a moisturizing stick

| | |
|---|---|
| Gellan gum | 2% |
| Xanthan gum | 1% |
| Sodium chloride | 1% |
| Ethanol | 1% |
| Polyurethane (SER-AD FX 1100) | 0.5% |
| Water | qs 100% |

The stick is prepared by mixing the constituents together at 80° C. with stirring and casting while hot.

The stick obtained is transparent and deposits a film which feels fresh when applied to the skin. In addition, it has good hardness (700 g/cm$^2$) and leaves a good deposit on the skin.

Comparative Example

The same composition as described above without polyurethane, which has a satisfactory hardness (800 g/cm$^2$), but leaves virtually no deposit on the skin.

The disclosure of French priority Application No. 9809793 filed Jul. 30, 1998 is hereby incorporated by reference into the present application Obviously, numerous modifications and variations of the present invention are possible in light of the above teachings. It is, therefore, to be understood that within the scope of the appended claims, the invention may be practiced otherwise than as specifically described herein.

What is claimed as new and is intended to be secured by letters patent is:

1. A solid composition, comprising:
   in an aqueous phase, a gelling system comprising (i) gellan gum, (ii) at least one other hydrocolloid selected from the group consisting of xanthan gum, carboxymethylcellulose, hydroxypropylcellulose, methylcellulose, hydroxypropyl-methylcellulose, hydroxyethylcellulose, agar-agar, carrageenans, alginates, carob gum, guar gum, gum arabic, karaya gum, gum tragacanth, ghatti gum, pectins, gelatin, caseinates and hydroxypropylguar, and (iii) at least one amphiphilic polymer comprising at least one fatty chain and at least one hydrophilic unit wherein said composition has transfer properties which allow deposition of an effective amount of a film onto the skin or lips.

2. The composition according to claim 1, wherein the hydrocolloid (ii) is selected from the group consisting of xanthan gum, carob gum, carboxymethylcellulose, hydroxypropylguar, and mixtures thereof.

3. The composition according to claim 1, wherein the gellan gum is present in an amount ranging from 1.5–15% by weight, based on the total weight of the composition.

4. The composition according to claim 1, wherein the amount of hydrocolloid (ii) ranges from 0.1–10% by weight, based on the total weight of the composition.

5. The composition according to claim 1, wherein the amphiphilic polymer comprising at least one fatty chain and at least one hydrophilic unit is selected from the group consisting of:
   (1) holosides modified with groups comprising at least one fatty chain;
   (2) copolymers of maleic anhydride or of a derivative thereof and of monomers comprising at least one fatty chain;
   (3) polyurethanes and derivatives thereof comprising groups comprising at least one fatty chain;
   (4) copolymers of crotonic acid and of monomers comprising at least one fatty chain;
   (5) copolymers of N-vinylpyrrolidone and of monomers comprising at least one fatty chain;
   (6) copolymers of (meth)acrylic acid and of monomers comprising at least one fatty acid chain;
   (7) nonionic copolymers of lower ($C_1$–$C_6$)-alkyl (meth)acrylate and of amphiphilic monomers containing a fatty chain; and
   (8) nonionic copolymers of hydrophilic (meth)acrylates and of hydrophobic monomers containing a fatty chain.

6. The composition according to claim 1, wherein the amount of amphiphilic polymer ranges from 0.05–20% by weight, based on the total weight of the composition.

7. The composition according to claim 1, wherein the gelling system comprising (i), (ii) and (iii) represents from 2–30% by weight, based on the total weight of the composition.

8. The composition according to claim 1, wherein the aqueous phase represents from 60–97% by weight based on the total weight of the composition.

9. The composition according to claim 1, which further comprises at least one salt and/or a solvent other than water.

10. The composition according to claim 1, wherein the amount of salt(s) ranges from 0.01–5% by weight based on the total weight of the composition.

11. The composition according to claim 9, wherein the amount of solvent(s) ranges from 0.01–20% by weight based on the total weight of the composition.

12. The composition according to claim 1, which further comprises at least one fatty phase.

13. The composition according to claim 12, wherein the amount of the fatty phase ranges up to 30% by weight based on the total weight of the composition.

14. A cosmetic or dermatological composition, comprising:
   the solid composition according to claim 1.

15. The composition according to claim 1, which further comprises at least one additive selected from the group consisting of antioxidants, free-radical scavengers, water-soluble or liposoluble dyes, fillers, lipophilic or hydrophilic active agents and fragrances.

16. The composition according to claim 1, which further comprises an active agent selected from the group consisting of hydrating agents, UV screening agents, antidandruff agents, conditioners, deodorant active agents, depigmenting agents, bleaching agents, tensioning agents and anti-wrinkle agents, latices and pseudolatices.

17. A make-up product, comprising:
   the composition according to claim 1.

18. A product for the care and/or conditioning and/or hygiene of the skin, mucous membranes, or the scalp, comprising the solid composition of claim 1.

19. A patch, comprising:
   the composition according to claim 1.

20. A process for the make-up of the skin and/or keratin fibers, which consists of:
   applying the solid composition according to claim 1 to the face, the lips, the contour of the eyes, the cheeks, the contour of the lips, and/or the eyelids.

21. A process for cosmetically treating the skin, the scalp and/or mucous membranes, consisting of:
   applying the solid composition according to claim 1 to the skin, the scalp and/or mucous membranes thereby caring for, conditioning or hygienically treating these portions of the body.

22. A transfer-free make-up product, comprising:
   the solid composition according to claim 1.

* * * * *